(12) United States Patent
Mundle et al.

(10) Patent No.: US 9,365,832 B2
(45) Date of Patent: Jun. 14, 2016

(54) PURIFICATION OF HERPES VIRUS

(71) Applicant: SANOFI PASTEUR BIOLOGICS, LLC, Cambridge, MA (US)

(72) Inventors: Sophia Mundle, Cambridge, MA (US); Stephen Anderson, Cambridge, MA (US); Simon Delagrave, Cambridge, MA (US)

(73) Assignee: SANOFI PASTEUR BIOLOGICS, LLC, Cambridge, MA (US)

( * ) Notice: Subject to any disclaimer, the term of this patent is extended or adjusted under 35 U.S.C. 154(b) by 0 days.

(21) Appl. No.: 14/369,844

(22) PCT Filed: Jan. 9, 2013

(86) PCT No.: PCT/US2013/020780
§ 371 (c)(1),
(2) Date: Jun. 30, 2014

(87) PCT Pub. No.: WO2013/106398
PCT Pub. Date: Jul. 18, 2013

(65) Prior Publication Data
US 2015/0004195 A1 Jan. 1, 2015

Related U.S. Application Data

(60) Provisional application No. 61/649,625, filed on May 21, 2012, provisional application No. 61/584,461, filed on Jan. 9, 2012.

(51) Int. Cl.
| | | |
|---|---|---|
| *B01D 15/04* | (2006.01) | |
| *C12N 7/00* | (2006.01) | |
| *B01D 15/36* | (2006.01) | |
| *C12N 1/02* | (2006.01) | |

(52) U.S. Cl.
CPC ............... *C12N 7/00* (2013.01); *B01D 15/363* (2013.01); *C12N 2710/16634* (2013.01); *C12N 2710/16651* (2013.01)

(58) Field of Classification Search
CPC ............. C07K 2319/02; C07K 16/087; C07K 16/088; B01J 49/0073; C02F 1/42; C02F 2001/422; C12N 2750/14151; C12N 2710/16651; C12N 7/00; C12N 2760/20251; C12N 2760/20252; C12N 7/02; A61K 35/763; Y10S 435/803; Y10S 435/948; Y10S 530/826; B01D 15/363; B01D 61/44; C07C 227/40
See application file for complete search history.

(56) References Cited

U.S. PATENT DOCUMENTS

| | | | |
|---|---|---|---|
| 6,267,967 B1 | 7/2001 | Johnston et al. | |
| 8,501,194 B2 * | 8/2013 | Spector et al. | 424/230.1 |
| 8,877,492 B2 * | 11/2014 | Delagrave et al. | 435/325 |
| 2008/0286850 A1 | 11/2008 | Liu et al. | |
| 2009/0325284 A1 | 12/2009 | Truran et al. | |
| 2010/0008944 A1 | 1/2010 | Knipe et al. | |
| 2010/0247573 A1 * | 9/2010 | Vellom et al. | 424/209.1 |
| 2011/0201087 A1 * | 8/2011 | Delagrave et al. | 435/235.1 |

FOREIGN PATENT DOCUMENTS

| | | |
|---|---|---|
| WO | 99/45104 A3 | 9/1999 |
| WO | 2004/112707 A2 | 12/2004 |

OTHER PUBLICATIONS

Grant Kyle, Dissertation submitted to the Graduate Faculty of Swanson School of Engineering in partial fulfillment of the requirements for the degree of Doctor of Philosophy, University of Pittsburgh, 2008, pp. 1-137.*

European Examiner Olivier Lonnoy, "Supplementary Partial European Search Report," issued Apr. 15, 2015 from corresponding European Application No. EP-13735764.6, 8 pages.

Hoshino, et al., "Protection from Herpes Simplex Virus (HSV)-2 Infection with Replication-Defective HSV-2 or Glycoprotein D2 Vaccines in HSV-1-Seropositive and HSV-1-Seronegative Guinea Pigs," J. Infectious Dis., vol. 200, No. 7, Oct. 1, 2009, pp. 1088-95.

Mundle, et al., "High-Purity Preparation of HSV-2 Vaccine Candidate ACAM529 Is Immunogenic and Efficacious In Vivo," PLOS One, vol. 8, issue 2, Feb. 2013, e57224, pp. 1-10.

O'Keeffe, et al., "The Affinity Adsorptive Recovery of an Infectious Herpes Simplex Virus Vaccine," Biotechnology and Bioengineering, vol. 62, No. 5, Mar. 5, 1999, pp. 537-545.

International Search Report and Written Opinion dated Mar. 11, 2013 from International Application No. PCT/US2013/020780, pp. 1-11.

* cited by examiner

*Primary Examiner* — Bao Li
(74) *Attorney, Agent, or Firm* — MH2 Technology Law Group, LLP (57) ABSTRACT

The present disclosure provides a method to prepare purified enveloped viral particle preparations employing ion exchange chromatography and tangential flow filtration.

16 Claims, 6 Drawing Sheets

PURIFICATION OF HERPES VIRUS

CROSS REFERENCE TO RELATED APPLICATIONS

This application claims the benefit of, and relies on the filing date of, U.S. provisional patent application No. 61/584,461, filed 9 Jan. 2012 and U.S. provisional patent application No. 61/649,625, filed 21 May 2012, the entire disclosures of which are herein incorporated by reference.

FIELD OF THE DISCLOSURE

This disclosure relates to methods for purifying viral particles and compositions comprising the same.

BACKGROUND OF THE DISCLOSURE

HSV-2 is the primary cause of infectious ulcerative genital disease worldwide, with HSV-1 becoming an increasingly important cause of genital herpes infection. Worldwide there are an estimated 23 million new HSV-2 infections per year. A number of HSV-2 vaccine approaches have been tested in the clinic (reviewed by Johnston C, et al., *J Clin Invest* 2011, 121:4600-4609) with varied degree of success. To address the lack of an effective vaccine, a replication defective HSV-2 vaccine strain virus (dl5-29, which has since been re-derived and renamed ACAM529 (Delagrave S, et al. PLoS ONE, 2012 7(10): e46714), also known as HSV529) has been constructed by deleting the $U_L5$ and $U_L29$ genes from the wild type virus (Da Costa X, et al., *J Virol* 2000, 74:7963-7971). The vaccine strain virus dl5-29 induces a protective immune response in vivo in mice and guinea pigs without either replication or establishment of latency (Da Costa X J, et al., *Proc Natl Acad Sci USA* 1999, 96:6994-6998; Hoshino Y, et al., *J Virol* 2005, 79:410-418; Hoshino Y, et al., *J Infect Dis* 2009, 200:1088-1095). Additionally, dl5-29 was shown to be effective in prevention of latent infection in guinea pigs irrespective of HSV-1 serostatus (Hoshino Y, et al., *J Infect Dis* 2009, 200:1088-1095). However, these studies were carried out with vaccine purified using centrifugation-based methods which are not readily scaled for commercial production. Indeed, a number of groups have defined laboratory-scale procedures for purification of herpes viruses based upon centrifugation (Arens M, et al., *Diagn Microbiol Infect Dis* 1988, 11:137-143; Lotfian P, et al., *Biotechnol Prog* 2003, 19:209-215); gradients (Goins W F, et al., *Methods Mol Biol* 2008, 433:97-113; Sathananthan B, et al., *APMIS* 1997, 105:238-246; Sia K C, et al., *J Virol Methods* 2007, 139:166-174; Szilagyi J F, et al., *J Gen Virol* 1991, 72 (PT 3):661-668); filtration (Knop D R, et al., *Biotechnol Frog* 2007, 23:715-721); and affinity chromatography (Jiang C, et al., *Biotechnol Bioeng* 2006, 95:48-57; Jiang C, et al., *J Virol* 2004, 78:8994-9006).

As with centrifugation-based methods, these other traditional laboratory-scale purification processes for vaccine strain viruses involve laborious procedures that cannot be scaled for commercial production of viral compositions prepared in accordance with World Health Organization (WHO) guidelines for human use, resulting in either low yields or insufficient purity (e.g., excessively high levels of residual host cell DNA). The World Health Organization (WHO) provides an upper limit of 10 ng host cell DNA per human dose, thus a need exists to provide virus preparations with less than 10 ng host cell DNA per human dose.

SUMMARY OF THE DISCLOSURE

The present disclosure provides a method to prepare purified enveloped viral particle preparations, including HSV particle preparations, employing ion exchange chromatography and tangential flow filtration. These purification methods can be used to prepare high yield viral preparations, including HSV preparations (e.g., HSV529), in accordance with WHO guidelines for human use, including high purity (e.g., less than 10 ng host cell DNA per exemplary human dose (e.g., $1 \times 10^7$ PFU)).

Preparation of the vaccine strain virus HSV529 by laboratory-scale virological methods (including sucrose cushion ultracentrifugation) results in crude material with greater than 2 mg of residual host cell DNA per $1 \times 10^7$ PFU of HSV529 (the World Health Organization limit is 10 ng DNA per human dose). The instant disclosure provides a method for purifying HSV529 in which the amount of residual Vero DNA is below 10 ng per $1 \times 10^7$ PFU of HSV529.

One aspect of this disclosure is directed to a method for the purification of herpes simplex virus (HSV) particles from a mammalian host cell culture comprising the steps of:
  a) treating the mammalian host cell culture with a viral releasing agent, such as dextran sulfate, to release the HSV particles from the host cells;
  b) treating the material from step (a) with an endonuclease, such as Benzonase®;
  c) filtering the material from step (b) to remove any intact cells or cellular debris;
  d) applying the solution obtained from step (c) to an anion exchange chromatography resin;
  e) eluting the HSV particles from the anion exchange column;
  f) subjecting the eluent from step (e) to tangential flow filtration; and
  g) recovering the purified HSV particles.

In some embodiments, the purified HSV particles contain greater than $1 \times 10^7$ or $2 \times 10^7$ PFU/mL. In other embodiments, the purified HSV particles contain less than 10 ng host cell DNA per $1 \times 10^7$ plaque forming units (PFU). In one embodiment, the HSV is a replication defective HSV, such as HSV529.

In yet another embodiment, the tangential flow filtration is a hollow fiber system. In one embodiment, the hollow fiber system has a molecular weight cutoff of 100 kDa. In another embodiment, the anion exchange chromatography comprises a membrane-based chromatography resin, such as the Mustang® Q (Pall Life Sciences) resin.

Another aspect of the disclosure is directed to a pharmaceutical composition comprising Herpes Simplex Virus (HSV) produced in a mammalian cell culture, said HSV isolated by the method comprising the steps of:
  a) treating the host cell culture with a viral releasing agent, such as dextran sulfate, to release HSV particles from the host cells;
  b) treating the product of step (a) with an endonuclease, such as Benzonase®, to reduce residual host cell DNA;
  c) filtering the product of step (b) to remove any intact cells or cellular debris;
  d) applying the filtrate of step (c) to an anion exchange chromatography resin;
  e) eluting the HSV particles from the anion exchange column;
  f) subjecting the eluent from step (e) to tangential flow filtration;
  g) recovering the purified HSV particles; and
  h) suspending the purified HSV particles in a pharmaceutically acceptable carrier.

In one embodiment, the quantity of host cell DNA in said composition is less than 10 ng host cell DNA per $1 \times 10^7$ plaque forming units (PFU). In another embodiment, the HSV is a replication defective HSV, such as HSV529. In other embodiments, the composition contains greater than $1\times10^7$ PFU/mL, preferably between about $1\times10^7$ to $2\times10^7$ PFU/mL.

Another aspect of the disclosure is directed to a composition comprising Herpes Simplex Virus (HSV) particles in a liquid stabilization buffer, wherein the liquid stabilization buffer comprises potassium glutamate, histidine, a salt, and a sugar. In one embodiment, the liquid stabilization buffer comprises 20-75 mM potassium glutamate, 1-20 mM histidine, 50-250 mM salt, and 5-20% sugar. In another embodiment, the liquid stabilization buffer comprises 50 mM potassium glutamate, 10 mM histidine, 160 mM salt, and 10% sugar. In one embodiment, the sugar is sucrose. In another embodiment, the pH of the liquid stabilization buffer is about 7.5. In one embodiment, the HSV is a replication defective HSV, such as HSV529. In another embodiment, the quantity of host cell DNA in said composition is less than 10 ng host cell DNA per $1\times10^7$ plaque forming units (PFU). In other embodiments, the composition contains greater than $1\times10^7$ PFU/mL, preferably between about $1\times10^7$ to $2\times10^7$ PFU/mL.

BRIEF DESCRIPTION OF THE FIGURES

FIG. 4 shows the results of optimization of purification conditions to achieve a yield of 400 human doses per NUNC cell factory. Each of the points on the curve represents the yield from an entire purification, starting with material which had been dextran sulfate-released from a single NCF of infected cell culture. HSV529 Purifications A-G were performed sequentially, with optimization of purification steps to improve yield and purity. The overall yield (y-axis; doses per NCF) increased with time as purification conditions were optimized. Flat sheet TFF was originally tested as an option for concentration and formulation of the partially purified vaccine virus (HSV529 Preparations A-D). Low step yield for flat sheet TFF (~20-40%) led to testing of hollow fiber TFF as an alternative (Preparations E-G), with dramatic improvement (~70-100% step yield) of recovery of infectious virus. Additionally, the high-capacity strong anion exchanger, Fractogel TMAE HiCap (BEAD, Preparation G) was tested as an alternative to Mustang® Q (MEMBRANE, Preparations A-F) as the bind-and-elute chromatography step.

FIG. 6 demonstrates that chromatography-purified HSV529 is as immunogenic and protective as sucrose cushion ultracentrifugation-purified HSV529. Panel A is a schematic representation of the animal study schedule, long labeled arrows represent viral inoculations (immunizations were performed sc and challenge was intravaginal) short arrows symbolize bleeds, hormone injection (DMPA=depot medroxyprogesterone acetate or Depo-Provera) and the study end day, as indicated. Panel B shows endpoint ELISA titers against a commercially available, purified HSV-2 viral lysate for immunized mice and Panel C depicts survival of animals as a % of the total (n=15 animals). Mice were immunized either with Mustang® Q (●)- or sucrose cushion (▲)-purified HSV529 or a placebo (♦) (PBS). Both vaccine preparations elicited similar anti-HSV-2 ELISA titers (Kruskal-Wallis Test P=0.99) and similar levels of protection against severe virus challenge with wild type HSV-2 strain 333 (Mantel-Cox Test P<0.0001).

DETAILED DESCRIPTION OF THE DISCLOSURE

In order to advance development of Herpes Simplex Virus (HSV) vaccines (e.g., HSV529) beyond animal models and into clinical studies, a scalable process capable of producing viral material suitable for human use was developed. A highly-purified, functional version of HSV529 was made by processing of infected complementing Vero cells (AV529-19) by a combination of dextran sulfate elution followed by endonuclease treatment, depth filtration, anion exchange chromatography and UF/DF (via tangential flow filtration). The overall yield for the optimized process is 10-20% of the infectious titer in the starting material, which equates to 100-300 doses per NUNC Cell Factory (NCF) (variability in the vaccine titer in the starting material accounts for the discrepancy between yield and number of doses purified per NCF). Importantly, this purification scheme yields virus that is sufficiently pure with respect to residual Vero genomic DNA for testing in humans (i.e., less than 10 ng residual host cell DNA per $1\times10^7$ PFU).

In one aspect, the present disclosure provides a method for the purification of an enveloped viral particle, such as a Herpes Simplex Virus (HSV) particle, from a mammalian host cell culture comprising the steps of:
  a) treating the mammalian host cell culture with a viral releasing agent (e.g., dextran sulfate) to release the enveloped viral particles from the host cells without significant lysis of the host cells;

b) applying the solution obtained from step (a) to an anion exchange chromatography resin;
c) eluting the enveloped viral particles from the anion exchange column;
d) subjecting the eluent from step (c) to tangential flow filtration, and
e) recovering the purified enveloped viral particles.

The present disclosure further provides a method for the purification of an enveloped viral particle, such as an HSV particle, from a mammalian host cell culture comprising the steps of:
a) treating the mammalian host cell culture with a viral releasing agent (e.g., dextran sulfate) to release the enveloped viral particles from the host cells without significant lysis of the host cells;
b) subjecting the solution obtained from step (a) to tangential flow filtration;
c) applying the retentate from the tangential flow filtration step to an anion exchange chromatography resin;
d) eluting the enveloped viral particles from the anion exchange column; and
e) recovering the purified enveloped viral particles.

The disclosure further provides a method as provided in the foregoing wherein before applying the solution obtained from step (a) to the anion exchange chromatography resin the solution obtained from step (a) is treated with an endonuclease (e.g., Benzonase®) to degrade residual host cell DNA.

The disclosure further provides a method as provided in the foregoing further comprising the step of clarifying the product material by depth filtration prior to anion exchange chromatography to remove any intact cells and/or cellular debris.

The disclosure further provides a method for the purification and the preparation of purified preparations of recombinant herpesvirus particles, in particular replication defective herpes simplex viral particles, such as HSV529 particles.

The viral (e.g., HSV) particles purified according to these methods are produced in high yield with sufficient purity that they can be administered to a human and preferably contain less than 10 ng residual host cell DNA per $1\times10^7$ PFU. In some embodiments, the purified viral (e.g., HSV) particles contain greater than $1\times10^7$ or $2\times10^7$ PFU/mL. In another embodiment, the purified viral (e.g., HSV, including but not limited to HSV529) particles contain about 10-20% of the infectious titer of virus in the solution obtained by treating the mammalian host cell culture with a viral releasing agent, such as Benzonase®.

The endonuclease is preferably one that degrades both DNA and RNA. In one embodiment, the endonuclease is a genetically engineered endonuclease from *Serratia marcescens* (Eaves, G. N. et al. *J. Bact.* 1963, 85, 273-278; Nestle, M. et al. *J. Biol. Chem.* 1969, 244, 5219-5225) that is sold under the name Benzonase® (EMD Millipore). The enzyme is produced and purified from *E. coli* strain W3110, a mutant of strain K12, containing the pNUC1 production plasmid (U.S. Pat. No. 5,173,418, which is hereby incorporated by reference in its entirety). Structurally, the protein is a dimer of identical 245 amino acid, ~30 kDa subunits with two important disulfide bonds. Benzonase® degrades all forms of DNA and RNA (single stranded, double stranded, linear and circular) and is effective over a wide range of operating conditions, digesting nucleic acids to 5'-monophosphate terminated oligonucleotides 2-5 bases in length. Benzonase® is produced under current good manufacturing practices (cGMP) and, thus, can be used in industrial scale processes for the purification of proteins and/or viral particles. Other endonucleases that are produced under cGMP conditions can likewise be used in the purification methods disclosed in this application.

In some embodiments, the purified preparations comprise viral particles, including HSV particles, in a liquid stabilization buffer. The liquid stabilization buffer may comprise, for example, potassium glutamate, at least one amino acid (e.g., histidine), at least one salt (e.g., sodium chloride), and/or at least one sugar (e.g., sucrose, trehalose, and/or sorbitol). An exemplary liquid stability buffer may comprise, for example, about 20-75 mM potassium glutamate (e.g., 50 mM potassium glutamate), about 1-20 mM histidine (e.g., 10 mM histidine), about 50-250 mM salt (e.g., 0.16 M sodium chloride), and about 5-20% sugar (e.g., 10% sucrose, trehalose, and/or sorbitol) at an appropriate pH (e.g., about any of pH 7.0, 7.1, 7.2, 7.3, 7.4, 7.5, 7.6, 7.7, or 7.8, especially about pH 7.5). Thus, for example, a suitable liquid stability buffer may comprise or consist of 50 mM potassium glutamate, 10 mM histidine, 160 mM sodium chloride, 10% sucrose, pH 7.5. In one embodiment, the HSV particle in the liquid stabilization buffer is a replication defective HSV, such as HSV529.

The disclosure further provides a pharmaceutically acceptable dosage form of an enveloped viral vector, such as a HSV vector, produced in a mammalian cell culture, said enveloped viral vector being isolated by a method comprising the steps of:
a) treating the host cell culture with a viral releasing agent (e.g., dextran sulfate) to release the enveloped viral particles from the host cells without significant lysis of the host cells,
b) treating the product of step (a) with an endonuclease (e.g., Benzonase®) to reduce residual host cell DNA;
c) filtering the product of step (b) to remove any intact cells or cellular debris;
d) applying the filtrate of step (c) to an anion exchange chromatography resin;
e) eluting the enveloped viral particles from the anion exchange column;
f) subjecting the eluent from step (e) to tangential flow filtration;
g) recovering the purified enveloped viral particles;
h) concentrating the viral particles by diafiltration; and
i) suspending the purified enveloped viral particles in a pharmaceutically acceptable carrier to a final concentration of greater than $1\times10^7$ PFU/mL.

In another embodiment, the final concentration is at least $2\times10^7$ PFU/mL. The disclosure further provides a pharmaceutically acceptable dosage form of an enveloped viral vector produced in a mammalian cell culture wherein the residual host cell DNA in said composition is less than 10 ng host cell DNA per $1\times10^7$ PFU. In one embodiment, the enveloped virus is a replication defective HSV, such as HSV529, as discussed in further detail below.

The viral particles obtained by the purification methods described herein retain infectivity following purification such that they can be used to induce a protective immune response when administered to a mammal. Thus, HSV529 particles purified according to the methods described herein induce a protective immune response when administered subcutaneously to BALB/c mice, as demonstrated in Example 10.

Typical mammalian cell hosts for enveloped viruses are well known to those of skill in the art and are readily available from public and private depositories. Particularly useful for the production of viruses exemplified here for purposes of the present disclosure include the Vero, HEK293, MDK, A549, EB66, CHO and PERC.6.

Herpes viruses include members of the genus herpesviridae including but not limited to HSV-1, HSV-2, varicella zoster virus, Epstein-Barr virus, and cytomegalovirus. Herpes Simplex Type-1 (HSV-1) and Type-2 (HSV-2) viruses are members of the alphaherpesvirus subfamily that cause prevalent, lifelong genital, dermal and ocular infections resulting in a spectrum of clinical manifestations that includes cold sores, genital ulceration, corneal blindness and encephalitis. Genital herpes simplex virus infection is a recurrent, lifelong disease with no cure, and no vaccines are available. While HSV-2 is the most common cause of genital ulcers, HSV-1 is becoming an increasingly important cause of genital herpes infection. HSV is an enveloped, linear, double-stranded DNA virus whose only known hosts are humans. HSV-1 and HSV-2 share 83% sequence homology of their protein-coding regions and the structure of their genomes are alike. They are distinguished by antigenic differences in the respective envelope proteins.

One example of a herpes virus useful in the practice of the present disclosure is HSV529 (previously known as dl5-29 and ACAM529), a replication-defective herpes virus (parent strain 186 syn+−1) genetically modified to contain 2 gene deletions: $U_L5$ and $U_L29$ as more fully described in Da Costa, et al (2000) J. Virology 74:7963-7971 and WO 99/06069, the disclosures of which are hereby incorporated by reference in their entirety. The original dl5-29 strain was re-derived and renamed as ACAM529 (Delagrave S, et al. PLoS ONE, 2012 7(10): e46714), which is also known as HSV529. Thus, the terms dl5-29, ACAM529 and HSV529 are used interchangeably throughout this application. The UL5 deletion consists of removal of the UL5 gene and part of the nonessential UL4 open reading frame (ORF) from nucleotides 12,244 to 15,143. The UL5 gene is an essential component of the viral helicase-primase complex and is required for viral DNA synthesis. The UL29 deletion consists of removal of the complete UL29 gene from nucleotides 58,784 to 62,527. The UL29 gene encodes the viral single-stranded DNA binding protein ICP8 (infected cell protein 8), which is essential for viral DNA synthesis. Together, this double mutation results in a virus that only grows on a complementary cell line, AV529-19 Vero cells containing the UL29 and UL5 genes and does not grow on normal Vero cells.

The strategy of introducing two mutations reduces the potential for generation of replication-competent virus due to recombination with endogenous gene in the propagating cell line or recombination with wild-type HSV in the host. Propagation of HSV529 on a large scale is achieved by growth of the virus under serum free conditions on its recombinant complementing cell line AV529-19 (derived from Vero CCL-81.2 (African green monkey) cells). HSV529 displays a similar pattern of protein expression on AV529-19 Vero cells compared to wild type virus on Vero cells with the exception that ICP8 is not expressed, and late proteins ICP5, gB, and ICP25, are expressed at lower levels compared to wild-type virus.

There is a range of time after infection of the host cells where the maximum amount of virus can be released from the cells. The timing of release varies depending on the temperature, the infection media used, the virus which was used to infect the cells, the container in which the cells were grown and infected and the cells themselves. Identification of this optimal harvest time is readily determined by sampling of the cell culture regularly over the conventional incubation period for the particular enveloped virus to determine the optimal yield. Under the conditions tested (Vero cells and HSV529), the maximum virus was released from the host cells between approximately 24 and 72 hours after infection.

Rather than harvesting the entire cell culture and lysing the host cells and attempting to isolate the newly produced viral particles from the complex cell milieu, it is preferred that the newly formed viral particles be isolated from the surface of the intact host cells. This can be accomplished by exposure of the host cells to a viral releasing agent. Such viral releasing agent is any agent that is capable of disruption of the interaction between the viral particle and the cell surface. In one embodiment, the viral releasing agent is dextran sulfate. In the practice of the present disclosure, the viral particles are preferably dislodged from the cell surface with solutions containing dextran sulfate, serum free media or phosphate buffered saline. In one embodiment, the viral releasing agent is a solution of the following components: 50 mM potassium glutamate, 10 mM histidine, 0.16 M sodium chloride, 100 μg/mL dextran sulfate MW 6-8 kDa, 10% sucrose, pH 7.5) (e.g., a liquid stability buffer further including dextran sulfate). It was determined experimentally that exposure of the cell culture to this viral releasing agent for 24 hours produced the highest yields. Based on experimentation, it is desirable that the culture be exposed to the releasing agent for at least 3 hours, at least 5 hours, at least 8 hours, or between 20 and 24 hours.

When performing a depth filtration procedure prior to anion-exchange chromatography, endonuclease treatment of the viral preparation prior to depth filtration improves the efficiency of the process by minimizing fouling of the depth filtration matrix. Alternatively, even in the absence of a depth filtration step, the recovery of virus from the chromatographic step was diminished when non-endonuclease treated virus was applied to this and other chromatographic supports.

As understood in the art, depth filtration refers to the use of a porous filter medium to clarify solutions containing significant quantities of large particles (e.g., intact cells or cellular debris) in comparison to membrane filtration which would rapidly become clogged under such conditions. A variety of depth filtration media of varying pore sizes are commercially available from a variety of manufacturers such as Millipore, Pall, General Electric, and Sartorious. In the practice of the disclosure as exemplified herein, SartoScale disposable Sartopure PP2, 0.65 μm depth filters (Sartorious Stedim, Goettingen, Germany) were used. Use of this system resulted in no appreciable loss of virus titer.

The principles of anion exchange chromatography are well known in the art, but, briefly, this method relies on the charge-charge interactions between the particles to be isolated and the charge on the resin used. Since most viruses are negatively charged at physiological pH ranges, the column contains immobilized positively charged moieties. Generally these are quaternary amino groups (Q resins) or diethylaminoethane groups (DEAE resin). In the purification of large particles such as viruses, it has been demonstrated that monolithic supports with large (e.g >1 micron) pore sizes permit purification of macromolecules such as viruses. Examples of commercially available anion exchange resins useful in the practice of the present disclosure include, but are not limited to, the Mustang® Q (Pall Life Sciences) and the Fractogel TMAE (Merck) resins.

Traditionally, anion exchange resins have been offered and used in the bead format, for example Q Sepharose™ available from GE Healthcare Bio-Sciences AB. Thus, in one embodiment, the anion exchange chromatography comprises a bead-based chromatography resin. However, throughput limitations of bead-based systems require large volume columns to effectively capture impurities. In bead-based chromatography, most of the available surface area for adsorption is internal to the bead. Consequently, the separation process is inherently slow since the rate of mass transport is typically controlled by pore diffusion.

In another embodiment, the anion exchange chromatography comprises a membrane-based chromatography resin, such as the Mustang® Q resin. Membrane-based chromatographic systems have the ligands attached directly to the convective membrane pores, thereby reducing the effects of internal pore diffusion on mass transport.

Tangential Flow Filtration (TFF) (also referred to as Cross Flow Filtration CFF) is well known to those of skill in the art and equipment and protocols for its implementation in a wide range of situations are commercially available from a variety of manufacturers including but not limited to the Pall Corporation, Port Washington, N.Y. and Spectrum Labs, Rancho Dominguez, Calif. Generally, TFF involves the recirculation of the retentate across the surface of the membrane. This gentle cross flow feed minimizes membrane fouling, maintains a high filtration rate and provides high product recovery. In one embodiment, the TFF step may be implemented with a flat sheet system, as exemplified herein. Flat sheet systems are generally preferred in large scale production where such systems are provided with a means (e.g., an open flow channel) to prevent excessive shear forces on the enveloped viral particles. Alternatively, the TFF step may be implemented with a hollow fiber system, as exemplified herein. In one embodiment, the Molecular Weight Cut Off (MWCO) of the TFF system is between 250-50 kDa, preferably about 200 kDa or 100 kDa.

Figure 1:
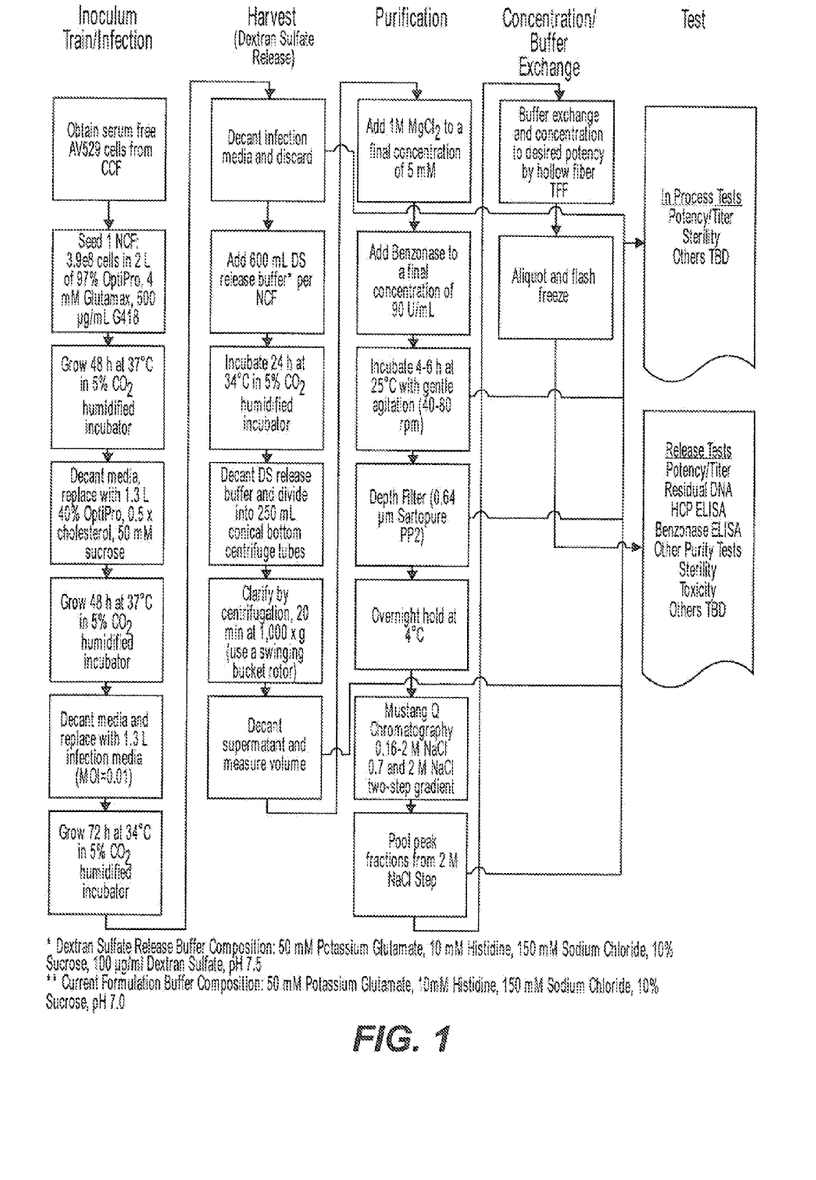
FIG. 1 provides a schematic representation of one embodiment of the present disclosure for the preparation of material comprising a replication deficient recombinant herpes virus known as HSV529 produced in complementing producer cell lines.

One embodiment of the present disclosure is directed to a method of preparing high-titer HSV529. After propagation of HSV529 in the complementing cell line, it is necessary to purify the virus from the cellular material and cell culture media components before further use. FIG. 1 represents a detailed flow diagram of an exemplary embodiment of the method. Briefly, at 72 hours post infection (hpi), the infection media is decanted from one or more NUNC cell factories (NCF's). A sterile, disposable funnel is placed into the NCF inlet port, and 600 mL of pre-warmed (34° C.) dextran sulfate elution buffer is poured into the NCF. The NCF is then flipped into the cap-up position and placed into a humidified, 5% $CO_2$ incubator at 34° C. for 24 h. After 24 h of incubation, the elution buffer is decanted from the NCF and clarified by centrifugation for 20 min. at 1,000×g in a centrifuge equipped with a swinging bucket rotor. The HSV529-containing supernatant is decanted and prepared for subsequent Benzonase® endonuclease digestion. If previously frozen, DS-released material is quick-thawed by placing at 37° C. The solution is adjusted to five mM $MgCl_2$ and ninety units of Benzonase® are added per mL of HSV529-containing solution. The solution should be incubated in a shake flask at 25° C., 80 rpm for 4-6 h. Prior to performing chromatography, the Benzonase®-treated solution is further clarified by depth filtration to remove any remaining cellular debris or aggregated material that could clog the chromatographic membrane. Chromatographic separation is performed by bind-and-elute anion exchange chromatography preferably utilizing the Mustang® Q membrane manufactured by Pall Life Sciences. Sodium chloride is utilized to elute bound HSV529 from the chromatographic support. Finally, concentration and formulation of HSV529 is performed, preferably by hollow-fiber tangential flow filtration (TFF) using a 100 kDa polysulfone (PS) hollow fiber module.

In the case of herpes virus particles, the size of the virus particle (200-250 nm) makes sterile filtration of the material difficult because the use of a standard sterilization filter (0.22 µm) results in a significant loss of material. For example, after filtering the HSV529 herpes virus through a 0.8 µm filter, 57.5% of infectious virus was recovered, in contrast to only 25.5% of the infectious virus that was recovered after filtering through a 0.45 µm filter. Thus, in the case of larger particles, like herpes virus particles, the process may be performed under sterile conditions.

Hydrodynamic shear stress played a role in the loss of infectious virus titer. In nearly all cases, when high-shear systems (closed channel flat sheet TFF and bead-based chromatographic support) are replaced by low-shear unit operations (open channel hollow fiber TFF and membrane-based chromatographic support) more infectious virus is recovered per step of the purification process. Without intending to be bound by any theory, it appears that convective liquid flow, as in the case of membrane (Mustang® Q) and monolithic (CIM) chromatographic supports, minimizes shear by eliminating flow vortices and turbulent eddies, which occur in the void space in traditional packed bead columns. Shear does not entirely explain recovery as is clear from the difference in yield of infectious virus from the membrane vs. the monoliths tested here.

Apart from optimization of chromatography, the most significant process change was from flat-sheet, closed-channel TFF to hollow fiber TFF. This resulted in up to a 10-fold increase in yield without compromising purity. Plaque assay results show that optimization of purification steps results in additional increases in yield without compromised purity in the case of the Mustang® Q anion exchanger. In contrast, Fractogel TMAE HiCap (a bead-based, strong anion exchanger)-purified material appears less attractive in that the final material contains about 2-fold more residual DNA and at least 2 orders of magnitude more dextran sulfate. Nevertheless, Fractogel TMAE HiCap might still be considered as a candidate chromatography resin because chromatography elution conditions could be optimized to improve purity.

Thus, the data reported in this application support the use of chromatography-based purification processes for preparation of HSV529, as well as other live-attenuated or replication-defective viral vaccines, suitable for testing in humans.

The herpes virus particles purified according to the present disclosure (e.g., enveloped viral particles contained within a liquid stability buffer) can be formulated according to known methods to prepare pharmaceutically useful compositions. The compositions of the disclosure can be formulated for administration to a mammalian subject, preferably a human, using techniques known in the art. In particular delivery systems may be formulated for intramuscular, intradermal, mucosal, subcutaneous, intravenous, injectable depot type devices or topical administration. When the delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration.

The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

In particular, such pharmaceutical preparations may be administered to mammalian subjects to induce an immune response in the mammalian subject. The intensity of such immune response may be modulated by dosage to range from a minimal response for diagnostic applications (e.g. skin testing for allergies) to a durable protective immune response (immunization) against challenge.

In order to enhance the immune response to the viral particle, such pharmaceutical preparations may optionally include adjuvants. Examples of adjuvants include aluminum salts (e.g. potassium aluminum sulfate, aluminum phosphate, aluminum hydroxyphosphate, aluminum hydroxide), 3D-MPL, oil-in-water emulsions including but not limited to AS03, AF03, AF04, MF-59, and QS21.

EXAMPLES

The following examples are to be considered illustrative and not limiting on the scope of the disclosure described above. The following Table 1 provides a summary of the reagents and materials used in the following examples.

TABLE 1

Reagent/Material Sources

| Component/Kit | Supplier | Catalog No. | Lot No. |
| --- | --- | --- | --- |
| Potassium Glutamate | Sigma | G1501 | 125K0170 |
| Histidine | Sigma | H6034 | 056K0002 |
| Sodium Chloride | Sigma | H7653 | 098K0098 |
| Multi-Compendial Sucrose | J. T. Baker | 4005-06 | E44627 |
| 1M Magnesium Chloride | G Biosciences | R004 | 072702 |
| Dextran Sulfate | Polydex | N/A | DS8-018R |
| Benzonase ® Endonuclease | EMD/Merck | 1.01697.0002 | K38806697 |
| Benzonase ® ELISA Kit | EMD/Merck | 1.01681.0002 | K92932881 |
| Vero HCP ELISA Kit | Cygnus Tech. | F500 | 8098 |
| Dextran Sulfate ELISA Kit | Lifespan Tech. | K-3800 | 6011 |
| 1 L 0.22 µm filter apparatus | Nalgene | 73520-986 (VWR) | na |
| 2 L PETG Bottle | Nalge/NUNC | 16159-138 (VWR) | na |
| 1 L PETG Bottle | Nalge/NUNC | 16159-136 (VWR) | na |
| 500 mL PETG Bottle | Nalge/NUNC | 16159-134 (VWR) | na |
| 250 mL PETG Bottle | Nalge/NUNC | 16159-132 (VWR) | na |
| 125 mL PETG Bottle | Nalge/NUNC | 16159-130 (VWR) | na |
| 1.5 mL Eppendorf Tubes | VWR | 20170-038 | na |
| 250 mL Centrifuge Tube | Corning | 430776 | na |
| Silicone MasterFlex Tubing (24) | Cole-Parmer | 96410-24 | na |
| Silicone MasterFlex Tubing (25) | Cole-Parmer | 96410-25 | na |
| 0.35 mL Mustang ® Q coin | Pall Life Sciences | MSTG18Q16 | na |
| 10 mL Mustang ® Q capsule | Pall Life Sciences | CLM05MSTGQP1 | IL6954 |
| SartoScale, SartoPure PP2 | Sartorius Stedim | 5595305PS-FF | 080620 |
| MidiKros Module (100 kDa, PS) | Spectrum Labs | X2AB-200-02P | 3241559 |

Stock Buffer Solutions:
Dextran Sulfate Elution Buffer (50 mM potassium glutamate, 10 mM histidine, 0.16 M sodium chloride, 100 µg/mL dextran sulfate MW 6-8 kDa, 10% sucrose, pH 7.5)
Stability Buffer/Column Equilibration Buffer (50 mM potassium glutamate, 10 mM histidine, 0.16 M sodium chloride, 10% sucrose, pH 7.0)
Step 1 Chromatography Elution Buffer (50 mM potassium glutamate, 10 mM histidine, 0.7 M sodium chloride, 10% sucrose, pH 7.0)
Step 2 Chromatography Elution Buffer (50 mM potassium glutamate, 10 mM histidine, 2 M sodium chloride, 10% sucrose, pH 7.0)
1 M sodium chloride
1 M magnesium chloride The following process is illustrative of the practice of the present disclosure in relation to the purification of the recombinant herpes virus HSV529. The process was carried out in five steps:
1. Dextran sulfate release of HSV529 from infected cells,
2. Benzonase® endonuclease digestion of residual DNA,
3. clarification by depth filtration (i.e., filtering to remove any intact cells or cellular debris),
4. bind-and-elute purification by anion exchange chromatography and
5. buffer exchange/concentration by tangential flow ultrafiltration/diafiltration (UF/DF).
Each of these steps is described in more detail below.

Example 1

Cells, Master Virus Seed, and Upstream Process

HSV529 production was accomplished by infection of a monolayer of complementing Vero cells (cell line AV529-19). Complementing cells were obtained as follows: African Green Monkey (Vero) ATCC cell line CCL-81.2 was stably transfected with plasmids pCId.UL5, pcDNA.UL29 and pSV2neo, which were provided by Dr. David Knipe (Harvard Medical School). Populations of cells were screened and clone AV529-19 was selected for its ability to best complement dl5-29 (as ACAM529 was previously known in the literature). The cell line has been grown and maintained in OptiPro (Life Technologies, Carlsbad, Calif.) supplemented with 4 mM glutamine (Hyclone, Logan, Utah) and 10% FBS (Life Technologies) at 37° C. in a 5% $CO_2$ atmosphere. Cell culture conditions for the purpose of infection and production of ACAM529 will be described below. The pre-master virus seed (preMVS) used to produce the ACAM529 master virus seed (MVS) was prepared in several steps from an original stock of dl5-29 as follows: the dl5-29 virus was propagated using complementing Vero cells, viral genomic DNA was extracted from the resulting virus and provided by Dr. David Knipe (Harvard Medical School) for transfection into AV529-19 cells, and the resulting virus amplified by a single passage. Viral genomic DNA was extracted from this amplified passage and transfected into AV529-19 cells under GLP conditions. The resultant virus was harvested, amplified by one passage, plaque-purified four times, amplified by passaging, and banked as the pre-MVS. The ACAM529 master virus seed (MVS) was prepared and banked under GMP using the pre-MVS and AV529-19.

Development was undertaken in order to determine upstream growth and infection conditions. Experiments were first performed at the small scale (12-well tissue culture plate and T125 flask) and eventually scaled up to production in NUNC cell factories (NCF's) with a working volume of 2 L and 6,320 cm$^2$ cell culture area. For clarity, upstream growth conditions are presented at the NCF scale. A single NCF was seeded with $3.8 \times 10^8$ serum-free AV529-19 cells in OptiPro media supplemented with 4 mM GlutaMAX (Life Technologies) and 500 µg/mL G418 (Life Technologies). The cells were grown at 37° C. in a 5% $CO_2$ humidified incubator, with a single medium change at 48 h to 1.3 L 40% OptiPro diluted in Dulbecco's phosphate buffered saline (DPBS) and supplemented with 0.5× cholesterol lipid concentrate (Life Technologies) and 50 mM sucrose. Cells were grown to confluence by incubation for an additional 48 h as above. At 96 h after seeding, the medium was decanted and replaced with 1.3 L of infection medium (40% OptiPro in DPBS with 0.5× cholesterol, 50 mM sucrose) and vaccine inoculum at a multiplicity of infection (MOI) of 0.01. Infection was allowed to proceed at 34° C. for 72 h (+/−4 h). Both MOI and time of harvest were optimized to ensure maximal production of HSV529.

Example 2

Ultracentrifugation-Based Purification Scheme

Prior to the development of the purification disclosed herein, the conventional method for purifying HSV involved ultracentrifugation. In the case where mechanical cell disruption was used to liberate HSV529 from the biomass, infected cells were detached from the substrate by manual disruption of the monolayer at 72 hours post infection (hpi). Cells were poured from the NCF and a cell pellet was prepared by centrifugation at 1,000×g. It was determined that at this point in the procedure it is possible to freeze the HSV529-containing cell pellet at −80° C. without an appreciable loss in titer, for storage prior to processing. The cell pellet from a single NCF was brought to 1 L with stabilization buffer (50 mM potassium glutamate, 10 mM L-Histidine, 160 mM NaCl, 10% sucrose, pH 7.0). The cell suspension was processed using a microfluidizer (Microfluidics Corporation, Newton, Mass.) at 3,000 psi, on ice to mechanically disrupt cells and shear cellular genomic DNA. The solution was adjusted to 5 mM $MgCl_2$ and 15,000 units of Benzonase® endonuclease (EMD/Merck, Darmstadt, Germany) were added to the HSV529-containing solution. The Benzonase® reaction was allowed to proceed at 25° C. for 4 h. The cellular lysate was then clarified by centrifugation at 5,000×g for 30 min at 4° C. Subsequently, the cleared cellular lysate was concentrated by flat sheet TFF on a Pellicon® XL50 microfiltration system (Millipore, Bedford, Mass.). Three Pellicon® XL50 cassettes (Biomax, 30 kDa, Polyethersulfone, 50 cm$^2$) were mounted on a Labscale™ TFF System (Millipore) using the multi-manifold accessory. The volume of the solution was reduced from ~1100 mL to ~50 mL. Throughout filtration, the inlet pressure was maintained at 30 psi, while back pressure was increased from 1 to 8 psi as needed to achieve a practical flux. Finally, the TFF retentate was subjected to ultracentrifugation for 4 h at 50,000×g and 4° C. over a 25% sucrose cushion, prepared in DPBS with $CaCl_2$ and $MgCl_2$. The HSV529-containing pellet was finally resuspended in stabilization buffer with 20% sucrose prior to being aliquoted, flash frozen on dry ice/ethanol and stored at −80° C. HSV529 prepared by this conventional, centrifugation-based method results in crude material with greater than 2 µg of residual host cell DNA per $1 \times 10^7$ PFU of HSV529.

Example 3

Dextran Sulfate

When mechanical cell disruption (sonication) was used prior to chromatographic separation the resultant virus was high in dsDNA, 0.33 or 2.0 µg/mL by dsDNA assay, for samples which either were or were not treated with Benzonase®, respectively) and the recovery of the virus was poor (12% recovery for Benzonase®-treated samples and 39% for those which had not been treated with Benzonase®) (see Table 2 below). Based on these results, a non-mechanical means to harvest the virus from the production cells was tested. Ultimately, dextran sulfate was selected as the best option for harvesting virus from the production cells. Testing with dextran sulfate was first conducted in small-scale, 12-well plates, followed by a scale up to NUNC Cell Factories (NFC).

12-Well Plates

In the small-scale testing, when cells exhibited ~100% cytopathic effect (CPE), as characterized by rounding of the cells, but remained attached (72 hpi) HSV529 was harvested by treatment with dextran sulfate. Initial development of the HSV529 viral harvest (dextran sulfate (DS) elution) procedure was performed in 12-well tissue culture plates. Parameters which were tested and/or optimized include: buffer (conditioned culture media, citrate and glutamate+histidine), pH (6.5-7.5), DS concentration (0-500 µg/mL), dextran sulfate molecular weight (5-5,000 kDa), degree of sulfation (dextran sulfate vs. heparin), temperature (34 and 37° C.), osmolality (0-30% sucrose), agitation (+/−), time (3, 5, 8 and 24 h) and timing (2-3 days post infection (dpi)) of release.

For screening purposes, infection medium was decanted from AV529-19 cells in 12-well plates at either day 2 or day 3 after infection. The medium was replaced with 600 µL of dextran sulfate elution buffer: stabilization buffer at pH 7.5 containing 0, 25, 50, 100, 200 or 500 µg/mL dextran sulfate (MW~5 kDa) (Polydex Pharmaceuticals, Toronto, Canada). The plates were incubated at 34° C. for 3, 5, 8 or 24 h before harvest. Dextran sulfate-released HSV529 was prepared for potency testing by centrifugation at 1,000×g to remove cells and cellular debris.

Figure 2A:
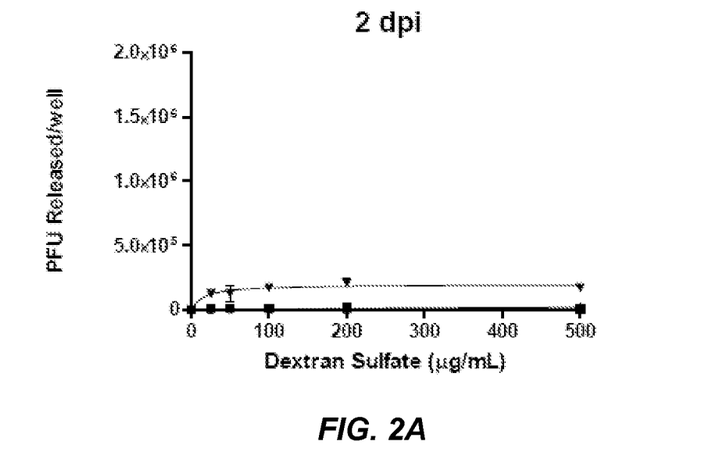
FIG. 2 shows the results of the chemical elution of HSV529 from the surface of infected AV529-19 complementing cells. The cell culture medium was decanted from confluent, infected AV529-19 cells grown in 12-well tissue culture plates and replaced with stability buffer containing 10% sucrose and 25-500 μg/mL dextran sulfate (DS). At 3 h (●), 5 h (■), 8 h (▲) and 24 h (▼) after the start of the dextran sulfate elution the samples were processed by centrifugation at 1,000×g and freezing at −80° C. prior to titration by plaque assay. The results represent the titer (PFU/mL) of the DS release supernatant, the error bars represent the standard deviation of the mean.
Figure 2B:
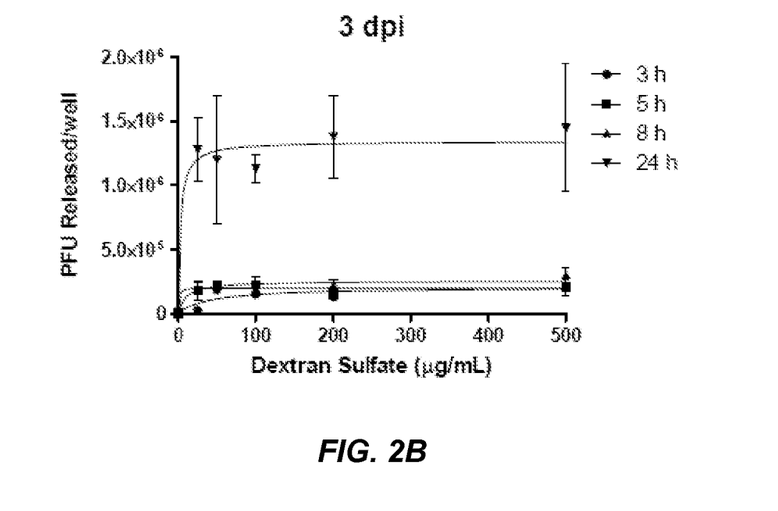

FIG. 2 shows the result of a single representative screening experiment to address whether HSV529 could be eluted from the surface of AV529-19 cells using dextran sulfate (DS). Indeed, when cells at 3 dpi were incubated with DS, one could detect infectious material in the supernatant after 24 h of incubation when ≥25 µg/mL of DS was used (FIG. 2B). A concentration of 100 µg/mL DS was selected for further studies.

NUNC Cell Factories

In the larger-scale testing, at 72 hours post infection (hpi), the infection media was decanted from a NCF into a container (2 L PETG Bottle) for disinfection and disposal, and a small aliquot was retained for potency testing. A sterile, disposable funnel was placed into the NCF inlet port, and 600 mL of pre-warmed (34° C.) Dextran Sulfate Elution Buffer (50 mM potassium glutamate, 10 mM histidine, 0.16 M sodium chloride, 100 µg/mL dextran sulfate MW 6-8 kDa, 10% sucrose, pH 7.5) was poured into the NCF. The NCF was placed on its side briefly, in order for the elution buffer to evenly distribute between the layers. The NCF was flipped into the upright position and placed into a humidified, 5% $CO_2$ incubator at 34° C. for 24 h. After 24 h of incubation, the elution buffer was decanted from the NCF into a 1 L PETG bottle. The liquid was then evenly distributed into 250 mL conical-bottomed centrifuge tubes and centrifugation was performed for 20 min. at 1,000×g in a centrifuge equipped with a swinging bucket rotor. The supernatant was decanted and placed into a fresh 1 L PETG bottle for subsequent Benzonase® endonuclease digestion. At this point in the procedure it is possible to quick freeze (on liquid nitrogen) the material for storage at −80° C. until future processing. Freezing was performed without agitation.

The optimized procedure for large (NCF) scale release of HSV529 from AV529-19 cells was as follows: at 3 dpi the infection medium was decanted; a sterile, disposable sterile funnel was placed into the NCF inlet port, and 600 mL of pre-warmed (34° C.) dextran sulfate elution buffer (stabilization buffer at pH 7.5 containing 100 µg/mL of DS with a MW of ~5 kDa) was poured into the NCF. The NCF was incubated 24 h in a humidified, 5% $CO_2$ incubator at 34° C. without agitation. After 24 h of incubation, the elution buffer was decanted from the NCF and clarified by centrifugation for 20 min at 1,000×g. It was determined that at this point in the procedure it is possible to freeze HSV529-containing harvest fluid at −80° C. without a loss in titer.

Example 4

Endonuclease Digestion

If previously frozen, dextran sulfate (DS)-released material from one NCF was removed from the −80° C. freezer and quick-thawed by placing in a 37° C. water bath. Gentle agitation by inversion was performed at ~10 min intervals to ensure that the sample did not overheat while melting. The volume of the material was measured and the solution was adjusted to 5 mM $MgCl_2$ using a 1 M $MgCl_2$ stock solution. Ninety units of Benzonase® were added per mL of HSV529-containing solution. The solution was gently mixed by inversion and placed in the incubator at 25° C., 80 rpm for 4-6 h.

Benzonase® endonuclease treatment of HSV529 substantially increases the purity of infectious virus after chromatography by Mustang® Q, as observed by agarose gel electrophoresis of purified virus with or without Benzonase® treatment (data not shown). The desirability of a Benzonase® endonuclease digestion step was confirmed at the small scale (about 20 mL). Nine (9) T225 flasks of infected AV529-19 cells were released by incubation with 100 µg/mL dextran sulfate (1926: 04). Released material was clarified by centrifugation at 2,000×g and the 193 mL supernatant was split into 2×96.5 mL aliquots. 1×96.5 mL was immediately filtered using 25 mm syringe filter units with low protein binding Supor membrane (a total of seven filters were used due to frequent fouling of the membrane). The 87.5 mL untreated sample was then applied to a 0.35 mL small scale Mustang® Q chromatographic membrane (coin) and eluted with a 160 mM-2M NaCl gradient in stability buffer, with manual hold steps to allow for elution of protein-containing material. The other aliquot was brought to 5 mM $MgCl_2$ and 90 U/mL Benzonase®. The solution was incubated for 4 h at room temperature (uncontrolled, on bench), and then held overnight at 4° C. Just prior to Mustang® Q chromatography the Benzonase-treated sample was filtered as above, 93.5 mL of sample was applied to the Mustang® Q coin and elution was performed as described previously (1926: 5-7). Individual elution fractions were analyzed by agarose gel electrophoresis (1.5%), SDS-PAGE (4-20% Tris-Glycine) and plaque assay.

At the small scale, dead end filtration of material which had not been treated by Benzonase® resulted in a ~50% recovery of infectious titer, whereas filtration of material post-Benzonase® treatment resulted in a much better (~100%) step yield. In contrast, more of the non-Benzonase®-treated material was recovered by Mustang® Q chromatography than Benzonase®-treated; ~95% as compared to ~75%, as shown in Table 2 below. Overall yield for each process was similar, but losses were sustained at different points along the downstream purification train. Based upon these observations, clarification of the bulk dextran sulfate-released material by depth or dead-end filtration should be performed after endonuclease treatment to prevent fouling of the filter and loss of titer. Additionally, Benzonase® treatment should be performed to ensure that final purified material is low in contaminating DNA.

Example 5

Depth Filtration

Prior to performing chromatography, the Benzonase®-treated solution is further clarified to remove any remaining intact cells or cellular debris or other aggregated material that might clog the chromatographic membrane. The depth filtration manifold was assembled as schematized below, using ¼" sterile flange fittings (tri-clover to hose-tail barb) (with the requisite gaskets and tri-clover clamps) as well as size 24 silicone MasterFlex tubing. The entire manifold, excluding pump, was autoclaved for 25 min. at 121° C. dry, as recommended by the manufacturer. The Benzonase®-treated sample was passed though the autoclaved depth filter at 50 mL/min, without pretreatment or preequilibration of the membrane. The membrane was vented until liquid was observed coming out of the vent. Depth-filtered material was collected in a sterile 1 L PETG bottle, and was stored at 4° C. overnight before chromatographic separation from contaminants.

Example 6

Anion Exchange Chromatography

At the NCF scale, the chromatography flowpath was assembled with size 25 silicone MasterFlex (Cole Parmer) tubing and 1½" sterile flange fittings (tri-clover to host-tail barb) with associated gaskets and tri-clover clamps. The flowpath, including the chromatographic membrane was prepared and chemically sterilized as per the manufacturers' instructions. Briefly, the membrane (10 mL Mustang® Q capsule, Pall Corporation, Port Washington, N.Y.) was wet with filter-sterilized reverse osmosis deionized (RODI) water while venting. Subsequently, the membrane was sterilized and preconditioned at 100-200 mL/min with 500 mL 0.5 M NaOH and 500 mL 1 M NaCl, respectively. Chromatography running buffer was comprised of stabilization buffer at pH 7.0 with the concentration of sodium chloride described for each step. The membrane was equilibrated with low salt (0.16 M NaCl) column equilibration buffer, until the pH and conductivity of the outlet stream matched that of the original buffer (~1.5 L of buffer). All subsequent chromatography steps were performed at 60 mL/min. Initially, the HSV529-containing sample was loaded onto the membrane, and a flowthrough fraction was collected, the membrane was then washed with equilibration buffer until the UV (280 nm) trace returned to baseline and a two-step salt elution was performed. Pre-elution of impurities was performed with 0.7 M NaCl-containing buffer. The pure, infectious, HSV529-containing fraction was eluted from the membrane with 2 M NaCl-containing buffer. Originally, infectious virus was eluted from the membrane in two steps (1.4 and 2 M NaCl). Subsequent analysis revealed that the two steps had comparable purity, and the higher salt concentration (2 M NaCl) was chosen to elute HSV529 in a single higher titer step. All fractions were collected manually while observing the absorbance at 280 nm on a chart recorder. An in-line digital pressure monitor was used to ensure that the pressure remained below 94 psig (maximum operating pressure).

Determination of the optimal chromatographic support for bind-and-elute chromatography was performed in a series of small-scale screening experiments, with the primary intention of attaining maximum yield of infectious virus in the eluted fraction. Table 2 below shows a non-exhaustive list of yields from such screening experiments.

TABLE 2

Virus step yield (PFU) from small-scale screening of anion exchange purification conditions (harvest method, chromatography resins, etc.)

| Harvest | Resin | Benzonase ® | Step Yield |
|---|---|---|---|
| Microfluidization | CIM ® DEAE | − | 5% |
| | CIM ® Q | − | 2% |
| Sonication | Capto ™ Q | − | 31% |
| | Capto ™ Q | + | 12% |
| | HiTrap ™ DEAE FF | − | 10% |
| | Mustang ® Q | − | 39% |
| | Mustang ® Q | + | 12% |
| Dextran Sulfate | Mustang ® Q | − | 95% |
| | Mustang ® Q | + | 75% |
| | Fractoge ®1 DEAE | + | 61% |
| | Fractogel ® TMAE | + | 59% |
| | Fractogel ® TMAE HiCap | + | 67% |
| | CIM ® DEAE | + | 15% |
| | CIM ® Q | + | 6% |
| | CIM ® EDA | + | 6% |
| | UNOsphere ™ Q | + | 22% |
| | Capto ™ Q | + | 65% |
| | GigaCap ® Q | + | 44% |

Figure 4:
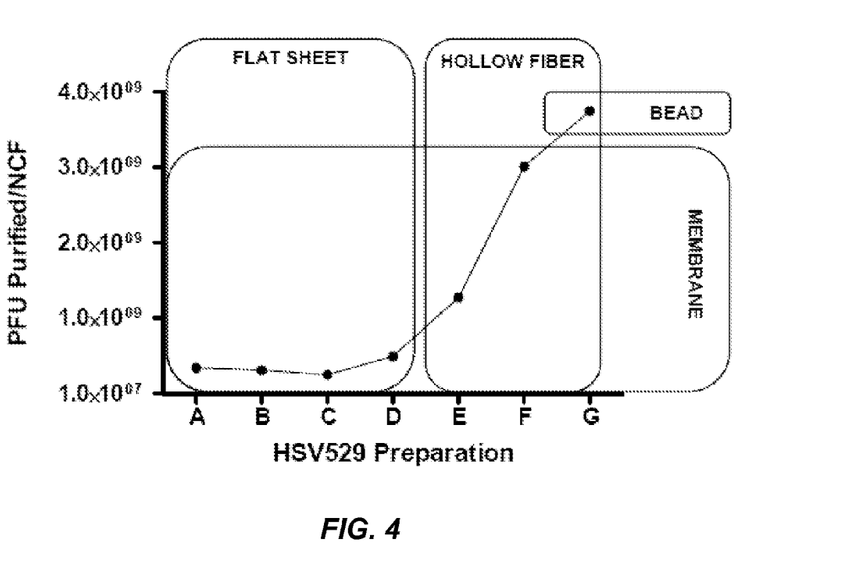
Figure 5A:
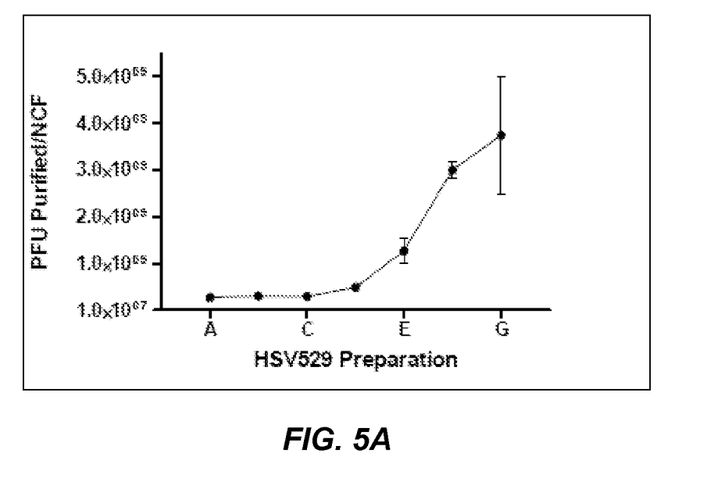
FIG. 5 shows the purity of HSV529 virus preparations. The tables provide superimposition of yield (●) (panel A) with purity (⊗) (panels B-D) results for HSV529 Preparations A-G. The right y-axes in panels B-D represent results from purity assays: residual Vero DNA qPCR, LOQ≤1 pg/μL (B), DS ELISA, LOD 3 ng/mL (C) and Vero HCP ELISA, LOD 2 ng/mL (D). In panel C, for preparations A-F, and panel D, preparation D, where no purity data point is present, the amount of impurity in the final material was below the assay-specific LOD. In all cases, the purity of Preparation F exceeded that of Preparation G, exemplifying why the Preparation F conditions were decided upon for use as the final purification scheme.
Figure 5B:
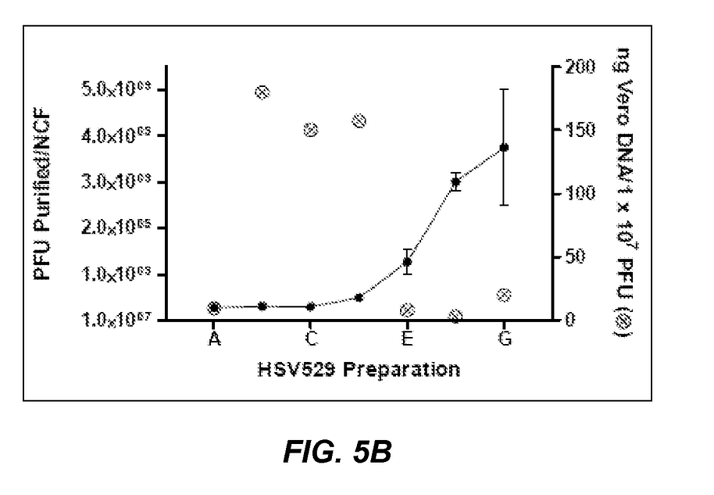
Figure 5C:
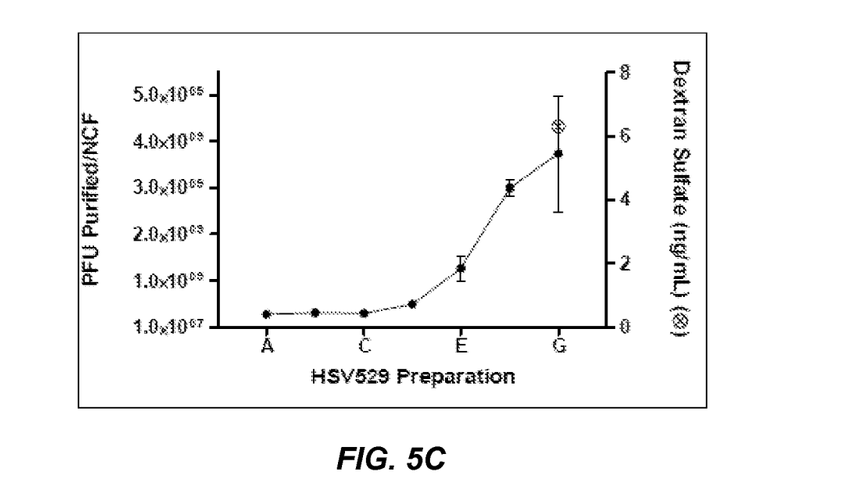
Figure 5D:
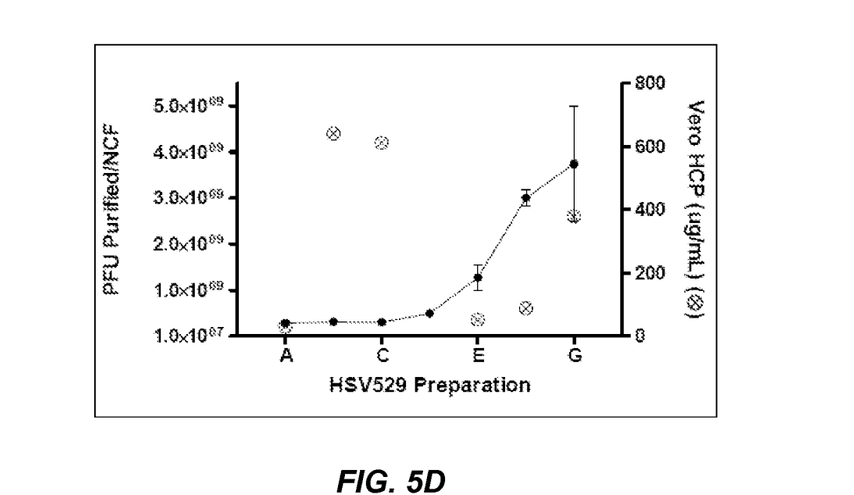

Overall yield (presented as the number of human doses (1×10⁷ PFU) per NCF) for HSV529 purifications from optimization experiments (labeled Preparations A-G) are presented as FIG. 4. The overall yield increased as chromatography and other purification conditions were optimized. Replacement of the Mustang® Q membrane-based anion exchanger with a bead-based tentacle resin (Fractogel TMAE HiCap, EMD Merck) resulted in a non-significant increase in yield and lower purity (compare HSV529 Preparations F and G in FIG. 5B-D).

Additional modifications tested in the small scale studies presented here include the use of dead end filtration (0.8 nm, 25 mm, supor membrane, syringe filter (Pall Corporation)) as a substitute for depth filtration and dialysis in Slide-a-Lyzer® cassettes (Thermo-Fisher Scientific (Pierce Protein Research Products), Rockford, Ill.) MWCO 10-20 kDa for buffer exchange instead of TFF.

While a wide variety of alternative approaches were attempted, ultimately dextran sulfate release, Mustang® Q and hollow fiber TFF were used for purification. Examples of chromatography chemistries and resins which were considered inadequate for reasons of yield or purity after assessment at small (20-50 mL) scale are as follows: HiTrap™ Heparin HP (GE Healthcare), Cellufine® Sulfate (CHISSO Corporation, Tokyo, Japan), HiTrap™ Capto™ Q (GE Healthcare), GigaCap® Q (TOSOH, Yamaguchi, Japan), UNOsphere™ Q (Bio-Rad, Hercules, Calif.), Fractogel® [DEAE, TMAE and TMAE HiCap] (EMD/Merck), CIM® [Q, DEAE, EDA, and SO₃] (BIASeparations, Villach, Austria), etc.

Figure 3:
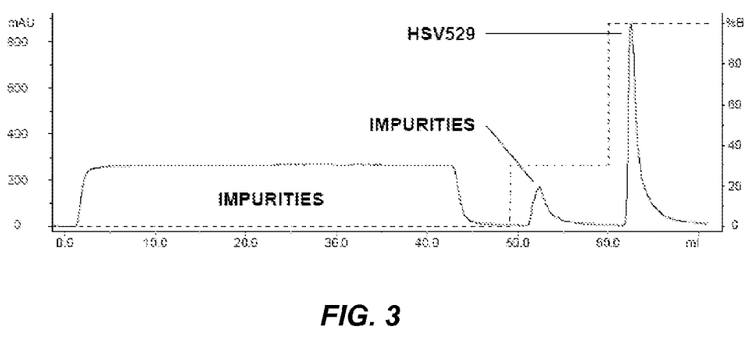
FIG. 3 shows the chromatographic profile during small scale (0.35 mL Mustang® Q coin) bind-and-elute purification of HSV529 by membrane-based anion exchange. The solid line represents the elution profile for absorbance at 280 nm, whereas the dotted line represents the concentration of salt as a percentage of the high salt buffer (Buffer B, 2 M NaCl). During the sample loading phase (0-50 mL) HSV529 bound the solid support, while unbound impurities passed through the column and were collected as the flowthrough fraction. Pre-elution of bound, non-viral protein impurities was achieved by applying a 700 mM NaCl (30% B) step over 30 column volumes (50-60 mL). Bound HSV529 was eluted from the column by step-wise increase of the salt concentration to 2 M NaCl (100% Buffer B) over 30 CV (60-70 mL).

Since the maximum yield was obtained with the Mustang® Q membrane, this was chosen for scale up to purification of material from a single NCF. FIG. 3 shows the chromatographic profile for elution of HSV529 (DS-harvested, Benzonase®-treated, and dead-end filtered) prior to loading onto the Mustang® Q coin (0.35 mL) on an AKTA Explorer (GE Healthcare, Piscataway, N.J.). The flow rate was 3 mL/min and step elution was performed automatically over 30 column volumes (CV). The HSV529 containing fraction is eluted from the support at 100% B or 2 M NaCl, as labeled.

Example 7

Concentration and Filtration

As noted above, FIG. 4 shows the results of a series of small-scale optimization experiments in which various purification parameters were altered to observe the effect on HSV529 yield. Major changes which positively impacted the yield are highlighted by boxes and include the switch from a flat sheet TFF system to a hollow fiber TFF system. Yield was effectively doubled by switching from flat sheet TFF with the Pellicon XL system to hollow fiber TFF with the Kros-Flo system (FIG. 4, horizontal boxes). It is thought that the increase in yield is due to a lower shear force being generated by open-channel flow as opposed to the flat sheet system where a turbulence generating screen in the flow path acts to maximize flux by minimizing formation of a gel layer. The hollow fiber TFF module which was used in the experiments presented here had a MWCO of 100 kDa, we also tested a 500 kDa MWCO cassette but yield was consistently lower than what is described here (data not shown).

At the NCF scale, the 2 M NaCl elution fraction was concentrated (5-10-fold by volume) and buffer-exchanged into the final formulation by diafiltration against 3-5× the volume of stabilization buffer containing 20% sucrose. This was performed by hollow fiber tangential flow filtration (100 kDa MWCO, 85 cm², polysulfone hollow fiber TFF module, Spectrum Laboratories, Rancho Dominguez, Calif.) on a Kros-Flo® Research II system, although in initial optimization experiments (labeled preparations A-D for the purposes of this report) flat sheet TFF was performed as described above. In order to minimize shear, the lowest suggested flow rate was utilized (130 mL/min, which equates to a shear rate of 4,000 s⁻¹). The transmembrane pressure (TMP) was kept below 4 psi throughout the diafiltration process to minimize formation of a gel layer, which could impede fluid flux. As before, the final HSV529-containing material was aliquoted, flash frozen on dry ice/ethanol and stored at −80° C. Due to the large size of the HSV-2 virus particle (180-200 nm), sterile filtration of the final material is not possible. For this reason, all manipulations should be performed under aseptic conditions.

Example 8

Titration of HSV529

Infectivity of HSV529 was assessed by titration of samples on the complementing cell line. 12-well tissue culture plates were seeded one day prior to inoculation with 4×10⁵ cells per well. Samples were serially diluted, plated and incubated 1 h, 37° C., 5% $CO_2$, with gentle rocking every 15 min. One mL of methyl cellulose overlay medium (in DMEM supplemented with L-glutamine, heat-inactivated FBS and antibiotics) was added to each well and the plates were incubated 48 h. Plaques were visualized by staining with 1% crystal violet in 70% methanol. After manual counting of plaques, titers were represented as plaque forming units (PFU)/mL.

Example 9

HSV529 Purity Assays (ELISA, qPCR, and PicoGreen dsDNA)

Commercially available ELISA was utilized to determine the purity of process retains as well as of purified HSV529. ELISAs against Benzonase® (EMD/Merck), Vero Host Cell Protein (HCP) (Cygnus Technologies, Southport, N.C.) and dextran sulfate (Lifespan Technologies, Salt Lake City, Utah) were used. Assays were performed as per the manufacturer's instructions, except that the following diluents were used in the sample preparation in cases where the diluent was not specified: Vero HCP ELISA (50 mM Tris, 0.1 M NaCl, 8 mg/mL bovine serum albumin, pH 7.0) and DS ELISA (1× phosphate buffered saline (PBS), pH 7.4). Assay specific limits of detection (LOD) are 0.1 ng/mL (Benzonase®), 2 ng/mL (Vero HCP) and 0.003 mg/mL (DS).

Residual Vero DNA testing of HSV529 samples was contracted to WuXI AppTec, Inc. (Philadelphia, Pa.) on a sample-by-sample basis. Briefly, the assay is a quantitative PCR (qPCR)-based GLP/GMP assay using ABI Fast 7500 Taqman® technology. Results were provided in the form of a final report, indicating the amount of residual Vero DNA for three nested ribosomal RNA amplicons of 102, 401 and 765 base pairs (bp). For the purposes of this study, the assay was performed at the research level (non-GMP). Data representing the 102 bp amplicon are presented in the results section of this report. The limit of quantitation (LOQ) for this assay is ≤1 pg/mL. Some samples were assayed for dsDNA content using the Quant-iT™ PicoGreen dsDNA Assay Kit (Invitrogen) as per the manufacturers instructions.

Mustang® Q-purified material (HSV529 Preparation F) contained less Vero residual DNA (FIG. 5B), dextran sulfate (FIG. 5C) and Vero HCP (FIG. 5D) than the Fractogel TMAE HiCap purified material (HSV529 Preparation G). To look more specifically at the benefits to using each step in the purification train, Tables 3 and 4 below highlight the yield and purity results for each step of the HSV529 Preparation A purification.

TABLE 3

| Retain | Yield (%) | DNA (ng/ dose) | Vero HCP (µg/ mL) | Benzonase® (ng/mL) | DS (µg/mL) |
|---|---|---|---|---|---|
| Start | 45 | a | 75 | <LOD | 28 |
| Benzonase® | 85 | a | 127 | 52 | 27 |
| Depth Filter | 108 | nd | 104 | 51 | 11.25 |
| Mustang ® Q FT | 0 | nd | 91 | 47 | <LOD |
| Mustang ® Q Wash | 0 | nd | 7 | 4 | <LOD |
| Mustang ® Q Step 1 | 0.1 | nd | 9 | <LOD | <LOD |
| Mustang ® Q Step 2 | 31 | <10 | 6 | <LOD | <LOD |
| Mustang ® Q Step 3 | 29 | <10 | 3 | <LOD | <LOD |
| TFF Permeate | 0 | nd | 0 | <LOD | <LOD |
| TFF Retentate | 38 | 9.74 | 30 | <LOD | <LOD |

TABLE 3-continued

| Retain | Yield (%) | DNA (ng/ dose) | Vero HCP (µg/ mL) | Benzonase® (ng/mL) | DS (µg/mL) |
|---|---|---|---|---|---|

[a]We were unable to determine the amount of Vero DNA in the starting material, as even at high dilutions there was 100% interference of qPCR signal by the sample (dextran sulfate and/or Benzonase ®).

TABLE 4

| Retain | Vero HCP (µg/mL) | Vero HCP (total mg) | (PFU/mg) | Purification Factor |
|---|---|---|---|---|
| Start | 75 | 75 | $1.5 \times 10^5$ | 1x |
| Benzonase ® | 127 | 75 | $1.2 \times 10^5$ | 1x |
| Depth Filter | 104 | 60 | $1.7 \times 10^5$ | 1x |
| Mustang ® Q FT | 91 | 53 | 0 | — |
| Mustang ® Q Wash | 7 | 3 | 0 | — |
| Mustang ® Q Step 1 | 9 | 1 | $3.4 \times 10^4$ | — |
| Mustang ® Q Step 2 | 6 | 1 | $9.2 \times 10^6$ | 60x |
| Mustang ® Q Step 3 | 3 | 0.3 | $3.1 \times 10^7$ | 200x |
| TFF Permeate | <LOD | — | — | — |
| TFF Retentate | 30 | 0.5 | $3.7 \times 10^7$ | 250x |

As previously mentioned, improvements to the yield (FIG. 4) were made by switching from flat sheet to hollow fiber TFF. Depth filtration appears to partially remove dextran sulfate from the feed stream, the rest of which is removed during chromatography (Table 3, column 6). Also, as was expected, Benzonase® was removed during chromatography as it does not bind to anion exchangers at neutral pH (Table 3, column 5). Although we were unable to determine the amount of Vero DNA in the starting material due to 100% interference of the qPCR signal by the sample (as measured by an internal E. coli DNA spike control), we were able to show that after Benzonase® treatment, depth filtration and chromatography, the amount of Vero DNA in the sample was less than the WHO limit per human dose of vaccine (Table 3, column 3). Finally, the majority of Vero HCP was removed during chromatography (flowthrough, wash and pre-elution; Table 3, column 4). Inspection of the purification factor (PFU per mg of Vero HCP) for HSV529-containing fractions shows a 250-fold purification of HSV529 with respect to Vero HCP (Table 4).

Example 10

Chromatography-Purified HSV529 is as Immunogenic and Protective as Sucrose Cushion-Purified HSV529 In Vivo All procedures were performed according to IACUC-approved protocols. Subcutaneous (sc) immunization of female BALB/c mice (Charles River, Wilmington, Mass.) 6-7 weeks old was performed in the scruff of the neck on days 0 and 21 of the study. On day 0, animals were injected with 100 µL sterile PBS (group 3) or with $1 \times 10^6$ PFU of HSV529, either sucrose cushion-purified (group 1) or chromatography-purified (group 2), diluted to 100 µL with sterile PBS. On day 34 of the study, mice were injected sc with 2 mg depot medroxyprogesterone acetate (Depo-Provera, DMPA) (SICOR Pharmaceuticals Inc., Irvine, Calif.) in PBS. Seven days later, mice were challenged intravaginally with 50 $LD_{50}$ ($8 \times 10^4$ PFU) of HSV-2 strain 333 in 20 µL with a positive displacement pipet. HSV-2 strain 333 was a generous gift from Dr. Jeffrey Cohen (NIAID, Medical Virology Section). Animals were observed for 14 days post challenge. Mice were euthanized upon observation of purulent genital lesions. Animals were bled on days 18, 35 and 41 of the study.

Endpoint ELISA titers against HSV-2 purified viral lysate (Advanced Biotechnologies, Colombia, Md.) were determined for serum from day 35 samples. Plates (96 well Maxisorp, Nalge NUNC International, Rochester, N.Y.) were coated with 100 μL/well of HSV-2 viral lysate at a concentration of 2 μg/mL. Serum IgG was detected with 1:2,000 biotin-anti-mouse IgG Fc (Sigma-Aldrich, Saint Louis, Mo.) diluted in 1% BSA, 0.05% Tween in PBS. Time resolved fluorescence (TRF) signal was measured using a Victor II fluorometer (Perkin Elmer, Waltham, Mass.) after addition of 0.1 μg/mL Dissociation-Enhanced Lanthanide Fluorescent Immunoassay (DELFIA) europium-streptavidin conjugate in DELFIA Assay Buffer.

Figure 6A:
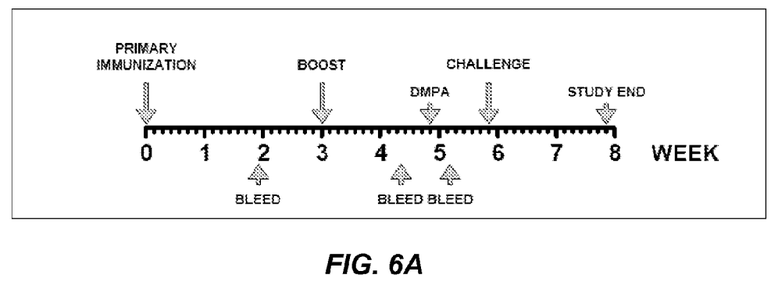
Figure 6B:
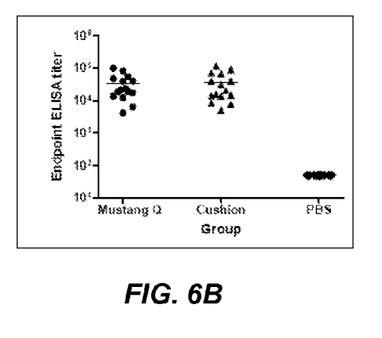
Figure 6C:
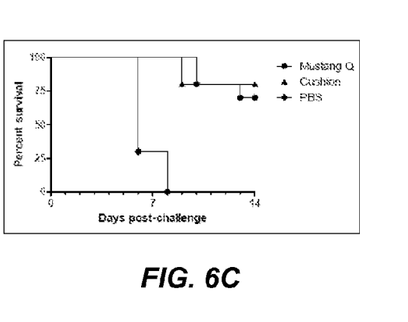

Female BALB-c mice were immunized subcutaneously with two doses of HSV529 prepared either by sucrose cushion ultracentrifugation or by chromatography (Preparation F). A lethal challenge study was carried out as schematized in FIG. 6A. Serum from blood taken one week after the second and final vaccine dose was tested for IgG response against a commercially available viral lysate. After two immunizations, both preparations elicit a similar anti-HSV-2 IgG response (FIG. 6B; P=0.99, one way ANOVA, Kruskal-Wallis test). Two weeks after the last immunization, animals were treated with medroxyprogesterone and, seven days later, given a 50×LD50 intravaginal challenge with wild type HSV-2 strain 333 (FIG. 6C). The sucrose cushion ultracentrifugation-purified vaccine and the chromatography-purified vaccine afforded statistically equivalent protection of 80% and 70%, respectively, while mock immunization resulted in complete lethality (0% survival; P<0.0001). A subsequent study with chromatography-purified HSV529 revealed that complete protection from challenge was achieved when immunization was performed intramuscularly.

It must also be noted that, as used in this disclosure and the appended claims, the singular forms "a", "an", and "the" include plural referents unless the context clearly dictates otherwise. Optional or optionally means that the subsequently described event or circumstance can or cannot occur, and that the description includes instances where the event or circumstance occurs and instances where it does not. For example, the phrase optionally the composition can comprise a combination means that the composition may comprise a combination of different molecules or may not include a combination such that the description includes both the combination and the absence of the combination (i.e., individual members of the combination). Ranges may be expressed herein as from about one particular value, and/or to about another particular value. When such a range is expressed, another aspect includes from the one particular value and/or to the other particular value. Similarly, when values are expressed as approximations, by use of the antecedent about, it will be understood that the particular value forms another aspect. It will be further understood that the endpoints of each of the ranges are significant both in relation to the other endpoint, and independently of the other endpoint. All references cited in this disclosure are hereby incorporated herein in their entirety.

What is claimed is:

1. A method for the purification of herpes simplex virus (HSV) particles from a mammalian host cell culture comprising the steps of:
   a) treating the mammalian host cell culture with a viral releasing agent to release the HSV particles from the host cells;
   b) treating the material from step (a) with an endonuclease;
   c) filtering the material from step (b) to remove any intact cells or cellular debris;
   d) applying the solution obtained from step (c) to an anion exchange chromatography resin;
   e) eluting the HSV particles from the anion exchange column;
   f) subjecting the eluent from step (e) to tangential flow filtration; and
   g) recovering the purified HSV particles.

2. The method of claim 1, wherein the purified HSV particles contain greater than $1\times10^7$ PFU/mL.

3. The method of claim 1, wherein the endonuclease is a genetically engineered endonuclease from *Serratia marcescens* produced and purified from *E. coli* strain W3110.

4. The method of claim 1, wherein the viral releasing agent is dextran sulfate.

5. The method of claim 1, wherein the purified HSV particles contain less than 10 ng host cell DNA per $1\times10^7$ plaque forming units (PFU).

6. The method of claim 1, wherein the HSV is a replication defective HSV.

7. The method of claim 6, wherein the replication defective HSV is HSV529.

8. The method of claim 1, wherein the tangential flow filtration is a hollow fiber system.

9. The method of claim 8, wherein the hollow fiber system has a molecular weight cutoff of 100 kDa.

10. The method of claim 1, wherein the anion exchange chromatography comprises a membrane-based chromatography resin.

11. A method for the large scale purification of herpes simplex virus (HSV) particles from a mammalian host cell culture comprising the steps of:
   a) treating the mammalian host cell culture with a viral releasing agent to release the HSV particles from the host cells;
   b) treating the material from step (a) with an endonuclease;
   c) filtering the material from step (b) to remove any intact cells or cellular debris;
   d) applying the solution obtained from step (c) to an anion exchange chromatography resin, wherein the anion exchange chromatography comprises a membrane-based chromatography resin comprising quaternary amino groups or diethylaminoethane groups;
   e) eluting the HSV particles from the anion exchange column;
   f) subjecting the eluent from step (e) to tangential flow filtration, wherein the tangential flow filtration is a hollow fiber system and wherein the hollow fiber system has a molecular weight cutoff of between 250-50 kDa; and
   g) recovering the purified HSV particles, wherein the purified HSV particles contain greater than $1\times10^7$ PFU/mL and less than 10 ng host cell DNA per $1\times10^7$ plaque forming units (PFU).

12. The method of claim 11, wherein in step (c) the material from step (b) is filtered with a porous filter medium.

13. The method of claim 11, wherein the HSV is a replication defective HSV529 and the mammalian host cell is a Vero cell line containing the UL29 and UL5 genes.

14. The method of claim 13, wherein 100-300 doses of purified HSV particles are recovered in step (g), wherein a dose of purified HSV is $1\times10^7$ PFU.

15. The method of claim 11, further comprising before step (a) a step of growing the mammalian host cell culture in a volume of at least 2 liters and a cell culture area of at least 6,320 $cm^2$.

16. The method of claim 13, wherein, the amount of Vero host cell protein following the elution step (e) is no more than 3 μg/mL.

* * * * *